US 8,861,815 B2
Oct. 14, 2014

(12) United States Patent
Cecchi et al.

(54) SYSTEMS AND METHODS FOR MODELING AND PROCESSING FUNCTIONAL MAGNETIC RESONANCE IMAGE DATA USING FULL-BRAIN VECTOR AUTO-REGRESSIVE MODEL

(75) Inventors: Guillermo Alberto Cecchi, New York, NY (US); Rahul Garg, Yorktown Heights, NY (US); Ravishankar Rao, Elmsford, NY (US)

(73) Assignee: International Business Machines Corporation, Armonk, NY (US)

(*) Notice: Subject to any disclaimer, the term of this patent is extended or adjusted under 35 U.S.C. 154(b) by 487 days.

(21) Appl. No.: 13/197,011

(22) Filed: Aug. 3, 2011

(65) Prior Publication Data

US 2013/0034277 A1 Feb. 7, 2013

(51) Int. Cl.
*G06K 9/00* (2006.01)
*G06K 9/62* (2006.01)
*A61B 5/05* (2006.01)
*G06T 7/00* (2006.01)
*G06F 19/00* (2011.01)
*G06T 11/00* (2006.01)

(52) U.S. Cl.
CPC ............ *G06F 19/345* (2013.01); *G06T 7/0012* (2013.01); *G06T 11/003* (2013.01); *G06F 19/321* (2013.01)
USPC ........... 382/128; 382/155; 382/159; 382/181; 600/416

(58) Field of Classification Search
CPC ................. G06K 2209/051; A61B 2576/026
See application file for complete search history.

(56) References Cited

U.S. PATENT DOCUMENTS

| | | | |
|---|---|---|---|
| 5,282,474 A | 2/1994 | Valdès Sosa et al. | |
| 7,092,748 B2 | 8/2006 | Valdes Sosa et al. | |
| 7,171,339 B2 | 1/2007 | Repucci et al. | |
| 8,532,756 B2 * | 9/2013 | Schalk et al. | 600/544 |
| 8,626,264 B1 * | 1/2014 | Beran | 600/407 |
| 2007/0027636 A1 | 2/2007 | Rabinowitz | |
| 2008/0091118 A1 | 4/2008 | Georgopoulos | |
| 2011/0022369 A1 * | 1/2011 | Carroll et al. | 703/11 |
| 2011/0028827 A1 * | 2/2011 | Sitaram et al. | 600/410 |

OTHER PUBLICATIONS

Desphande et al., "Multivaraite Granger Causality analysis of fMRI data", Human Brain Mapping 30:1361-1373, 2009.*
Formisano et al., "Multivariate analysis of fMRI time series: classification and regression of brain responses using machine learning", Magnetic Resonance Imaging 26: 921-934, 2008.*
Rubinov et al., "Complex network measures of brain connectivity: uses and interpretations", NeuroImage 52: 1059-1060, 2010.*

(Continued)

*Primary Examiner* — Anand Bhatnagar
*Assistant Examiner* — Soo Park
(74) *Attorney, Agent, or Firm* — Vazken Alexanian; Ryan, Mason & Lewis, LLP

(57) ABSTRACT

Systems and methods for modeling functional magnetic resonance image datasets using a multivariate auto-regressive model which captures temporal dynamics in the data, and creates a reduced representation of the dataset representative of functional connectivity of voxels with respect to brain activity. Raw spatio-temporal data is processed using a multivariate auto-regressive model, wherein coefficients in the model with high weights are retained as indices that best describe the full spatio-temporal data. When there are a relatively small number of temporal samples of the data, sparse regression techniques are used to build the model. The model coefficients are used to perform data processing functions such as indexing, prediction, and classification.

13 Claims, 6 Drawing Sheets

(56) References Cited

OTHER PUBLICATIONS

G.A. Cecchi et al., "Inferring Brain Dynamics Using Granger Causality on fMRI Data," 5th IEEE International Symposium on Biomedical Imaging: From Nano to Macro (ISBI), May 2008, pp. 604-607.

A. Roebroeck et al., "The Identification of Interacting Networks in the Brain Using fMRI: Model Selection, Causality and Deconvolution," NeuroImage, Sep. 2009, 7 pages.

P.A. Valdés-Sosa et al., "Estimating Brain Functional Connectivity with Sparse Multivariate Autoregression," Philosophical Transactions of the Royal Society B, Biological Sciences, May 2005, pp. 969-981, vol. 360, No. 1457.

Pedro A. Valdés-Sosa, "Spatio-Temporal Autoregressive Models Defined Over Brain Manifolds," Neuroinformatics, 2004, pp. 239-250, vol. 2, No. 2.

M.K. Carroll et al., "Prediction and Interpretation of Distributed Neural Activity with Sparse Models," NeuroImage, Jan. 2009, pp. 112-122, vol. 44, No. 1.

O. Yamashita et al., "Sparse Estimation Automatically Selects Voxels Relevant for the Decoding of fMRI Activity Patterns," NeuroImage, Oct. 2008, pp. 1414-1429, vol. 42, No. 4.

\* cited by examiner

SYSTEMS AND METHODS FOR MODELING AND PROCESSING FUNCTIONAL MAGNETIC RESONANCE IMAGE DATA USING FULL-BRAIN VECTOR AUTO-REGRESSIVE MODEL

FIELD OF THE INVENTION

The present invention relates generally to systems and methods for modeling and processing functional magnetic resonance image datasets and, more specifically, systems and methods for modeling functional magnetic resonance image datasets using a multivariate auto-regressive model which captures temporal dynamics in the data, and creates a reduced representation of the dataset representative of functional connectivity of voxels with respect to brain activity.

BACKGROUND

Recent advances in medical imaging technology have introduced functional magnetic resonance imaging (fMRI) capable of acquiring sequences of images of brain activity by measuring changes in blood oxygenation levels. Functional magnetic resonance imaging is increasingly used in the medical field to scan subjects, both normal and diseased. The fMRI data is a 4-dimensional dataset involving 3 spatial dimensions and one temporal dimension. An fMRI dataset is very large and difficult to visualize for making meaningful conclusions. Typically, this data is processed by different analysis techniques to generate a number of "human viewable maps" which are then used to study the fMRI data and reach conclusions.

One of the most common approaches to processing fMRI data is known as the general linear model (GLM) technique, which makes use of an experimental protocol while a subject is being scanned. The GLM technique produces spatial maps of brain activity, which indicate those areas of the brain that are active for a given experiment (stimulus) being conducted on the target subject. More specifically, with the GLM technique, activity in different regions of while the subject is not conducting the given experimental task. A thresholding protocol or linear analysis is then performed on each dataset to determine if certain measured activity is beyond noise. Once spatial maps of brain activity are obtained for the measured activity with and without the experimental stimulus, the spatial maps are compared to determine which areas of the brain are differentially activated.

With the GLM protocol, the resulting spatial maps only provide information based on measured activity of different regions of the brain, independent of each other, and do not provide any information regarding how activity in one voxel relates to, or affects, or otherwise triggers, activity of another voxel. In other words, the spatial maps derived using the GLM technique do not provide any information about the dynamics of ongoing brain activity which is not directly related to the experimental task conducted. Therefore, it is not possible to fully summarize the fMRI data using such techniques and later use it for indexing, prediction, or classification purposes.

SUMMARY OF THE INVENTION

Aspects of the present invention generally include systems and methods for modeling functional magnetic resonance image datasets using a multivariate auto-regressive model that captures temporal dynamics in the data, and creates a reduced representation of the dataset representative of functional connectivity of voxels with respect to brain activity. More specifically, aspects of the invention include systems and method that fit raw spatio-temporal data with a multivariate auto-regressive model. This model captures the temporal dynamics in the data, and creates a reduced representation of the data. Coefficients in the model with high weights can be retained as indices that best describe the full spatio-temporal data. When there are a relatively small number of temporal samples of the data, sparse regression techniques are used to build the model. The model coefficients are used to perform data processing functions such as indexing, prediction, and classification.

More specifically, in one aspect of the invention, a method to perform an image data processing operation includes obtaining a raw spatio-temporal dataset acquired from scanning a brain of a subject performing a given task, constructing a full spatio-temporal model using the raw spatio-temporal dataset, wherein the full spatio-temporal model represents brain activity that occurs in all regions of the subject's brain in response to the subject performing the given task, selecting model parameters from the full spatio-temporal model which meet or exceed a threshold parameter that defines a level of causal relation between voxels in the acquired dataset, generating a reduced model representation of the full spatio-temporal model using the selected model parameters, generating a vector representing the reduced model, and using the vector to perform an image data processing operation.

In another aspect of the invention, a method for predicting future brain activity includes obtaining a previously generated spatio-temporal model representing brain activity of a subject, which model was previously generated from scan data collected with the subject performing a given task, initializing the previously generated spatio-temporal model with current brain activity data derived from a scan of the subject's brain while the subject is performing the same given task, and predicting future brain activity of the subject using the previously generated spatio-temporal model based on the current brain activity data initializing said model. The biofeedback may be provided to the subject based on the predicted future brain activity to provide an indication to the subject of the predicted future brain activity of the subject.

In accordance with another aspect of the invention, an apparatus for modeling and processing image data is provided. An apparatus includes a memory and a processor coupled to the memory, wherein the apparatus is operative to perform methods for modeling and processing image data as described above.

In accordance with yet another aspect of the invention, a computer program product to perform an image data processing operation is provided. The computer program product comprises a computer readable storage medium having computer readable program code embodied therewith. The computer readable program code comprises computer readable program code configured to perform methods for modeling and processing image data as described above.

These and other aspects, and features of the present invention will become apparent from the following detailed description of illustrative embodiments thereof, which is to be read in connection with the accompanying drawings.

DETAILED DESCRIPTION OF THE PREFERRED EMBODIMENTS

Figure 1:
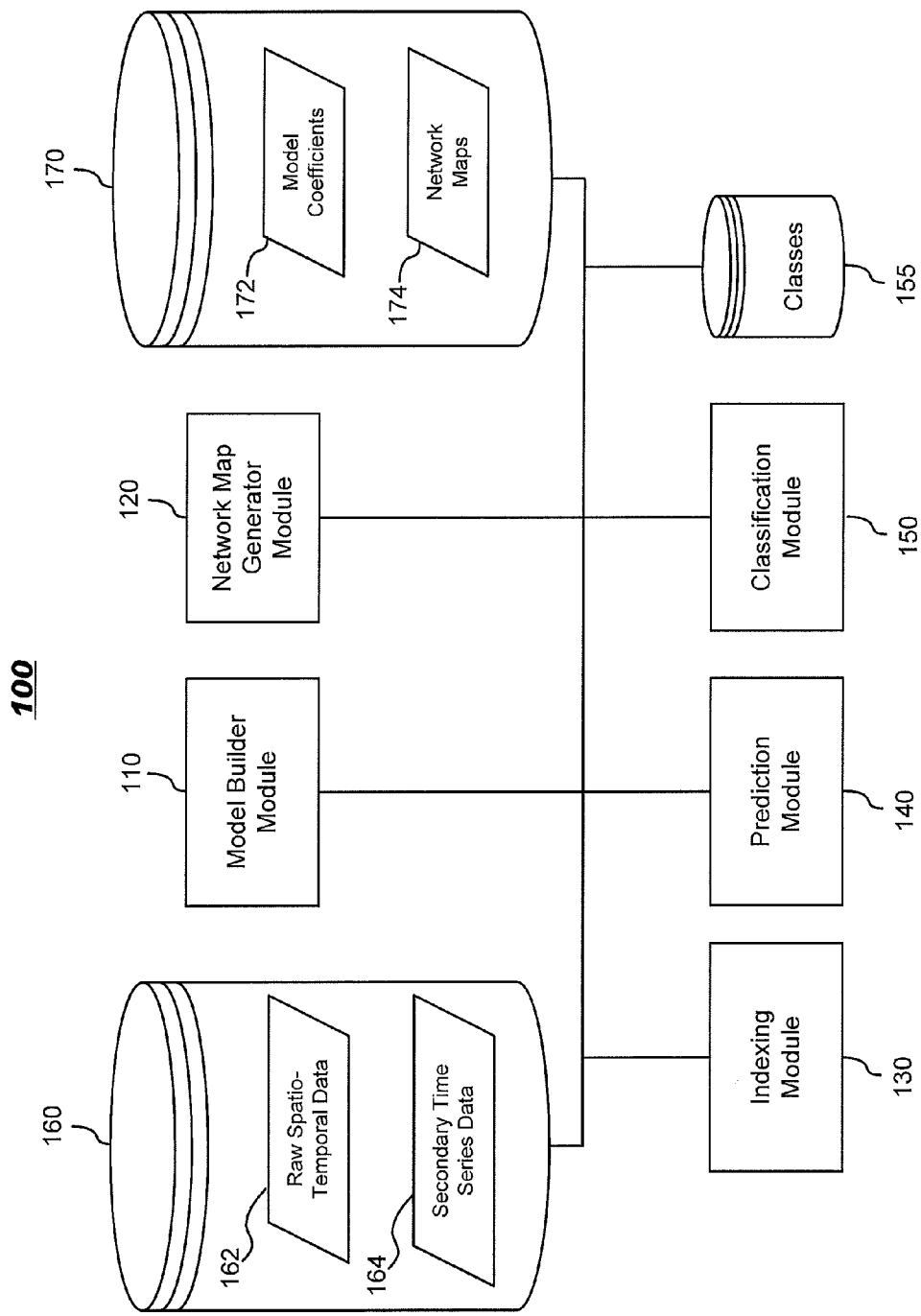
FIG. 1 is a high-level block diagram of a system for modeling and processing functional magnetic resonance imaging data according to an aspect of the invention.

Aspects of the present invention generally include systems and methods for modeling functional magnetic resonance image datasets using a multivariate auto-regressive model that captures temporal dynamics in the data, and creates a reduced representation of the dataset representative of functional connectivity of voxels with respect to brain activity. More specifically, aspects of the invention include systems and method that fit raw spatio-temporal data with a multivariate auto-regressive model. This model captures the temporal dynamics in the data, and creates a reduced representation of the data. Coefficients in the model with high weights can be retained as indices that best describe the full spatio-temporal data. When there are a relatively small number of temporal samples of the data, sparse regression techniques are used to build the model. The model coefficients are used to perform data processing functions such as indexing, prediction, and classification.

Magnetic Resonance Imaging (MRI) is an imaging technique to visualize the internal structure and/or function of a body. MRI provides higher contrast between the different soft tissues of the body than provided by many other imaging techniques. Consequently, MRI is useful in neurology and brain imaging. MRI is also useful for imaging other portions of the body, for example, musculoskeletal, cardiovascular, and for oncological (cancer) imaging. MRI does not use ionizing radiation, but uses a powerful magnetic field to align the nuclear magnetization of, for example, hydrogen atoms in water in the body. Radio frequency (RF) fields are used to systematically alter the alignment of this magnetization, causing the hydrogen nuclei to produce a rotating magnetic field detectable by the scanner. This signal can be manipulated by additional magnetic fields to build up enough information to construct an image of the body or portions thereof.

Functional magnetic resonance imaging (fMRI) is a type of specialized MRI. fMRI, for example, measures the hemodynamic response (i.e., response to the dynamic regulation of the blood flow in the brain) related to neural activity in the brain or spinal cord of humans or other animals. Neurons require energy to function. This energy is supplied in the form of glucose and oxygen carried in hemoglobin. The blood supply of the brain is dynamically regulated to give active neural assemblies more energy while inactive neural assemblies receive less energy. Therefore, changes in blood flow and blood oxygenation in the brain (collectively known as hemodynamic) are closely linked to neural activity. When nerve cells are more active they consume more oxygen carried by hemoglobin in red blood cells from local capillaries. The local hemodynamic response to this oxygen utilization is an increase in blood flow to regions of increased neural activity, occurring after a delay of, for example, 1-5 seconds. This local hemodynamic response may rises to a peak over, for example, 4-5 seconds before falling back to near baseline levels, leading to local changes in the relative concentration of oxyhemoglobin and deoxyhemoglobin and changes in local cerebral blood volume in addition to this change in local cerebral blood flow. Therefore, fMRI may, for example, produce images of brain activity by measuring changes in blood oxygenation levels and/or other hemodynamic responses.

A voxel is a volume element, representing a value, a structure, or a three-dimensional image on a three-dimensional grid. A voxel is analogous to a pixel, which represents two-dimensional image data. Voxels are frequently used in the visualization and analysis of medical and scientific data. As with a pixel, a voxel itself typically does not comprise spatial position or coordinates of the voxel. Rather, spatial position of a voxel is inferred based on the position of the voxel relative to other voxels (e.g., the position in the data structure that makes up a single volume image). The word voxel is a linguistic blend of the words volumetric and pixel.

Embodiments of the invention are useful, for example, in processing large amounts of data, such as data produced in conjunction with or analysis of functional magnetic resonance imaging (fMRI). fMRI measurements can give rise to large amounts of data, for example, consisting of tens of thousands or hundreds of thousands of voxels and/or hundreds or thousands of samples, for example, time points or samples. According to aspects of the invention, fMRI may be used to scan the brains of subjects, for example, while the brains are receiving stimuli or when brains are diseased or have other states.

According to aspects of the invention, fMRI data (e.g., time-series data collected at each voxel) may be used to predict the brain, mental or cognitive state of a subject, for example, an emotion (e.g., anger, happiness, sadness, anxiousness, or annoyance); extract patterns of or predict a mental disease, for example, schizophrenia, depression, Alzheimer's or dementia; discriminate between mental or brain states of a person, for example brain or mental states associated with a person looking at a face or at a building, a person listening to a phrase in a first language or a phrase in a second language, a person performing a mental or physical task or different mental or physical tasks, or a person having one or other emotion; and predicting brain activity given a specific stimulus or specific stimuli (e.g., auditory such as words or sounds, visual such as pictures, or activity of a person such as playing a video-game).

FIG. 1 is a high-level block diagram of a system for modeling and processing functional magnetic resonance imaging data according to an exemplary embodiment of the invention. The system 100 comprises a plurality of computational modules including a model builder module 110, a network map generator module 120, an indexing module 130, a prediction module 140, and a classification module 150. In addition, the system 100 comprises a storage system comprising databases 155, 160, and 170. The database 160 stores raw spatio-temporal datasets 162 that are acquired by fMRI time series scans and other secondary time series datasets 164 from secondary sources (such as breathing, motion, experimental protocol etc.).

The model builder module 110 processes the raw spatio-temporal data 162 and secondary time series data 164 associated with a dataset of a full brain scan of a given subject using a multivariate auto-regressive process to generate a full brain vector model of brain activity for a subject brain. In one exemplary embodiment, when there are a relatively small number of temporal samples of the data, sparse regression techniques are used to build the model. The model builder module 110 generates model coefficients 172 for the full brain scan, which are stored in the database 170.

The network map generator module 120 (or network graph generator module) processes the full set of model coefficients 172 of a given dataset and generates a reduced representation of the dataset in the form of network maps 174 (or network graphs) that are stored in database 170. As explained below with reference to FIG. 3, these network maps can be generated in the form of directed node graphs, where each node represents a voxel and where a directed edge (or link) between nodes indicates the degree to which a parent node (voxel) exerts a causal influence on a child node (voxel). In general, to generate these node graphs, the network map generator module 120 can identify coefficients in the full model representation having high weights (using one or more techniques as discussed below), and then retain the coefficients as indices that best describe the full spatio-temporal data to generate the network maps 174 (or network graphs). One exemplary method for generating a reduced representation of a full spatio-temporal model of brain activity of a subject, which is implemented by the network map generator module 120, will be discussed below with reference to FIG. 4.

The network maps 174 include a summary of the fMRI datasets of various scans, and are used by the various modules 130, 140, and 150 for indexing, prediction, and classification. For example, the indexing module 130 uses the network maps 174 to find fMRI datasets from stored in database 160 which are similar to a given fMRI dataset. The indexing methods implemented by the indexing module 130 may be used for locating one or more stored datasets of brains that are functionally similar to a target brain, or one or more stored datasets brains that perform a same or similar task while being scanned as the target brain. The indexing module 130 can process search requests, whereby a given search request (database query) is used to match the model coefficients of the given brain with the model coefficients stored in the database. The datasets matching the given model coefficients are returned as the query results. One exemplary method for performing a database search using a vector representation of a reduced spatio-temporal model of brain activity of a subject, which is implemented by the indexing module 130, will be discussed in further detail below with reference to FIGS. 5 and 6, for example.

The prediction module 140 implements methods to determine future fMRI brain activity in a given voxel using the past information of activity in other voxels and secondary information. The secondary information may include breathing rate, heart rate, subject motion, information from an experimental protocol, and/or any other information about subject activity. The prediction module 140 can also implement methods to predict future secondary information using past values of voxel activity and secondary information. In particular, this includes prediction of subject's future brain activity using past data. The autoregressive model can also be used by the prediction module 140 to make predictions of the future activity (in fMRI voxels as well as secondary data). The model coefficients can be used to create a variety of maps such as "prediction power", "prediction accuracy", "impulse response function," and other various types of maps. One exemplary method for predicting future brain activity using a reduced representation of a full spatio-temporal model of brain activity of a subject, which may be implemented by the prediction module 140, will be discussed in further detail below with reference to FIG. 8, for example.

The classification module 150 processes various network maps 174 to create classes 155 of datasets that can be used to classify a new dataset into one of various predefined groups. The different groups or classes 155 may include, e.g., healthy brain vs. diseased brain classes, male vs. female classes, etc. The network maps 174 are used by the classification module 150 to build a classifier for discriminating among the different groups or classes 155. One exemplary method for performing classification using a vector representation of a reduced spatio-temporal model of brain activity of a subject, which may be implemented by the classification module 150, will be discussed in further detail below with reference to FIG. 7, for example.

Figure 2:
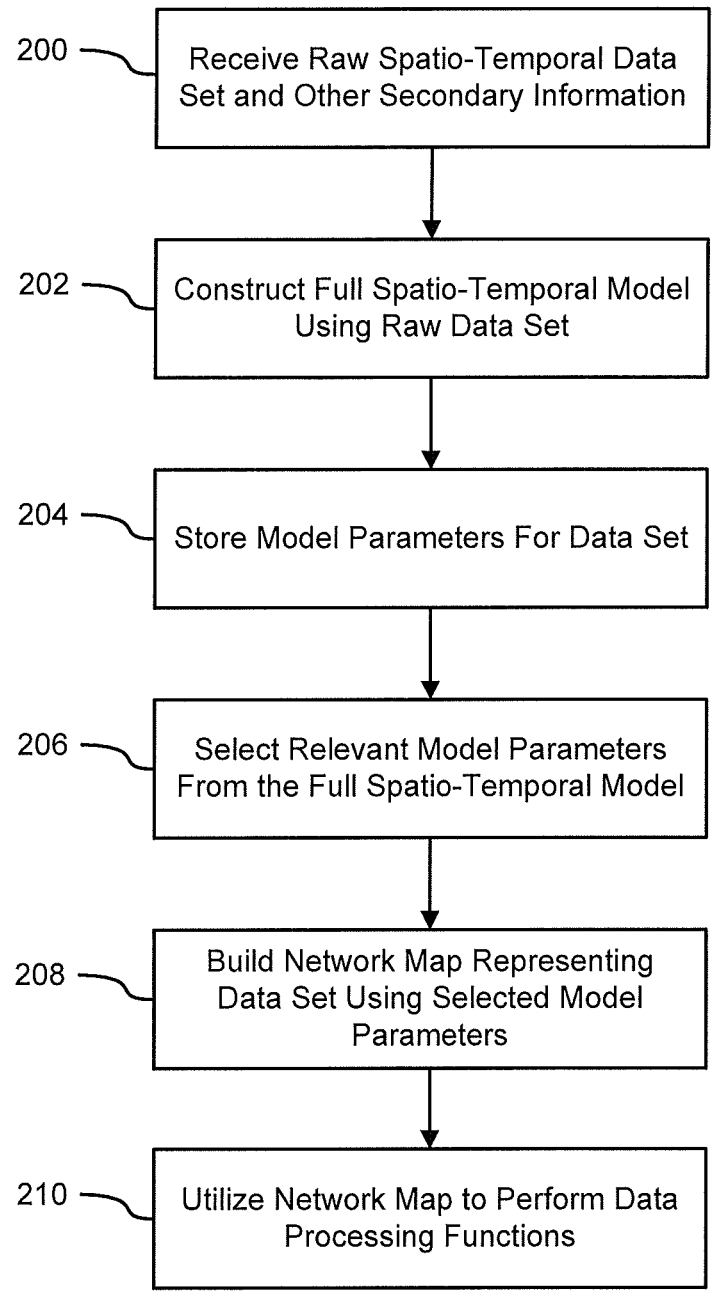
FIG. 2 is a flow diagram of a method for modeling and processing functional magnetic resonance imaging data according to an aspect of the invention.

FIG. 2 is a block diagram of a method for modeling and processing functional magnetic resonance imaging data according to an exemplary embodiment of the invention. In particular, FIG. 2 illustrates an exemplary mode of operation of the system of FIG. 1. Initially, the model builder module 110 receives a raw spatio-temporal dataset and possible other secondary information acquired for a given brain scan of a subject (step 200). The model builder module 110 constructs a full spatio-temporal model of the brain using the raw data set (step 202). As discussed in further detail below, in one aspect of the invention, a multivariate autoregressive modeling process is used to build a full brain model using the raw spatio-temporal dataset.

Once the model is built, the complete set of model parameters of the data set are stored for further processing (step 204). Using one or more techniques as discussed below, a set of relevant model parameters from the full spatio temporal model are selected to generate a reduced, but accurate, representation of the full spatio-temporal model (step 206). The selected set of model parameters is then used to build one or more network maps (step 208). In various aspects, the network maps include directed node graphs that model the functional connectivity of a set of voxels within the full brain scan. The network maps represent causal relations between voxels in the brain and represent dynamics of the modeled process of brain activity. These network maps are used then used to perform data processing functions (step 210) including indexing, classification and prediction, as discussed herein.

Building a Full-Brain Model

In one aspect of the invention, the process depicted in step 202 of FIG. 2 as implemented by the model builder module 110 in FIG. 1 includes a process for building a full model of brain activity using an autoregressive model, as will be discussed now in further detail below. In a preferred embodiment of the invention, a stochastic process modeling the brain activity X (represented as a N dimensional row vector) is modeled as a linear combination of its past values and independent, identically distributed (iid) noise. Such representation is also called a multivariate autoregressive model. Formally, this model is as follows:

$$X(t) = \sum_{\tau=1}^{k} X(t-\tau) A(\tau) + E(t) \qquad (1)$$

where k is called the model order, $A(\tau)_{\tau=1,\ldots,k}$ are the model parameters in the form of k matrices of size N×N (with coefficients $a_{ij}(t)$), E(t) is an N-dimensional row vector of noise with zero mean and a covariance equal to R. For any $t_1 \neq t_2$, $E(t_1)$ and $E(t_2)$ are identically distributed and uncorrelated.

In this model, if $a_{ij}(t) > 0$ for some t, then past values of $X_i$ improve the predictability of $X_j$ and therefore, $X_i$ is said to have causal influence on $X_j$. The parameter t is called the causality lag between $X_i$ and $X_j$.

To infer the causal relationships in the linear simplification, we need to know the model parameters $\{a_{ij}(t)\}$. The model parameters may be estimated from a realization of the process X using an fMRI time series dataset. Let $\{x(t)\}_{t=1,\ldots,T}$ be a realization of the stochastic process X and $\{e(t)\}_{t=1,\ldots,T}$ be a realization of the iid noise E. This realization must satisfy:

$$x(t) = [x(t-1) \ldots x(t-k)][A'(1) \ldots A'(k)]' + e(t) \quad (2)$$

for all $t \in [k+1, \ldots T]$. The above set of equations can be written in compact matrix form as follows.

Let Y be a matrix of size (T−k)×N, Z be a matrix of size (T−k)×Nk, W be a matrix of size Nk×N, and $\aleph$ be a matrix of size (T−k)×N obtained by stacking the rows in equation (2) for t=T−k+1 to t=T. Now, Eq. 2 may equivalently be written as:

$$Y = ZW + \aleph \quad (3)$$

where Y and Z are derived from a realization x of the process X, W=[A'(1) ... A'(k)]' contains all the model parameters ($a_{ij}(t)$) and $\aleph$ is derived from realization e of the noise E.

The maximum likelihood estimate ($W_{MLE}$) of model parameters can be determined by the standard least square solution of Eq. (3), i.e., $$W_{MLE} = \underset{W}{\arg\min} \sum_{j=1}^{N} \|Y_j - ZW_j\|_2^2 = \quad (4)$$

$$\underset{a_{ij}(\tau)}{\arg\min} \sum_{j=1, t=k+1}^{N,T} \left[ x_j(t) - \sum_{\tau=1}^{k} \sum_{l=1}^{N} x_l(t-\tau) a_{lj}(\tau) \right]^2 \quad (5)$$

where $Y_j$ represents the $j^{th}$ column of Y and $W_j$ represents the $j^{th}$ column of W. Eq. (4) has a unique solution only if (3) is not under-determined, i.e.:

$$(T-k)N \geq N^2 K \Rightarrow T \geq (N+1)k.$$

In general, for reliable estimates of the model parameters, Eq. (3) must be sufficiently over determined, i.e., the number of observations of the process X must be significantly larger than the number of model parameters ($(T-k)N \gg N^2 k$).

If the model is sparse, i.e., the number of non-zero coefficients in $\{a_{ij}(\tau)\}$ is significantly smaller than the total number of coefficients (Nk), then it might be possible to find a reliable solution to (3) using techniques of sparse regression, as follows.

In particular, consider a multivariate linear regression model of the form Y=ZW where Y is a known $n_1 \times 1$ response vector, Z is a known $n_1 \times n_2$ regressor matrix and W is the unknown model vector of size $n_2 \times 1$ to be determined using the response Y and regressor Z. Common methods to solve this include standard least square regression, ridge regression, and subset selection methods. For these techniques, it is usually required to have $n_1 \gg n_2$. However, there is a growing body of work indicating that if W is sparse, then it may be recovered even if $n_2 > n_1$ using a lasso regression technique, such as described in R. Tibshirani, "Regression Shrinkage and Selection via the Lasso.", Journal of the Royal Statistical Society, Serial B, 58(1):267-288, 1996, which is incorporated herein by reference. The lasso regression process solves the problem:

$$\min_{W} \|Y - ZW\|_2^2 \quad (6)$$

$$\text{s.t.} \quad \|W\|_1 \leq t \quad (7)$$

where $\|.\|_2^2$ represents the square of L2 norm and represents the L1 norm of the respective vectors. The parameter t is the regression parameter that is usually chosen after cross-validation.

It can be verified that for any t, there exist a $\lambda$ such that the program (6, 7) is equivalent to the following optimization problem:

$$\min_{W} \|Y - ZW\|_2^2 + \lambda \|W\|_1 \quad (8)$$

The programs (6, 7) and (8) can be solved efficiently using a technique called least angle regression in time no longer than time required to carry out the ordinary least square computation. The least angle regression method is known in the art and described in the paper: B. Efron, et al.; *Least Angle Regression*; the Annals of Statistics 2004; vol. 32(1), pages 407-499, the disclosure of which is incorporated herein by reference.

The estimation of multivariate autoregressive coefficients in (3) may be viewed as a regression problem where Y is the response variable, Z is the matrix containing the regressors and W is the model to be determined. In this case, the maximum likelihood estimate of (4) becomes the least square solution to the regression problem. The lasso formulation thus becomes:

$$W^{sparse} = \underset{W}{\arg\min} \sum_{j=1}^{N} [\|Y_j - ZW_j\|_2^2 + \lambda \|W_j\|_1] \quad (9)$$

Note that the coefficients of $W_j$ only appear in the $j^{th}$ term of the above sum. Therefore, this problem may be decomposed into N independent lasso regression problems of size (T−k)× Nk as follows:

$$W_j^{sparse} = \underset{W_j}{\arg\min} \|Y_j - ZW_j\|_2^2 + \lambda \|W_j\|_1$$

The goodness of fit of the regression is captured using the notion of which predictability ($p_j$) is defined as:

$$p_j = 1 - Q \Sigma_{t=k+1}^{T} [x_j(t) - \Sigma_{\tau=1, l=1}^{k, N} x_l(t-\tau) a_{lj}(\tau)]^2$$

where:

$$Q = [\Sigma_{t=k+1}^{T} (x_j(t))^2]^{-1}$$

It may be verified using the properties of the lasso regression that the predictability varies from 0 to 1. If the predictability of a voxel is 1, the time course of that voxel can be predicted exactly using the past k values of other voxels. On the other hand, if a voxel has zero predictability, then the time course of that voxel is orthogonal to (independent of) the shifted time course of all the other voxels.

Selecting Model Parameters to Generate Reduced Model

Once a full-brain multi-variate autoregressive model of brain activity is obtained using techniques described above, the model may be processed in various ways to implement functions such as database indexing, classification and/or prediction of brain activity. In one aspect of the invention, a full spatio-temporal autoregressive model of brain activity can be represented in the form of a three-dimensional directed node graph comprising a plurality of voxels or nodes say $V_i$, where i is an index, and edges $a_{ij}(1)$ where $a_{ij}(1)$ is a link between voxels $V_i$ and $V_j$. The value "1" within the parenthesis, e.g., (1) represents the order of the model. With an order of "1", a lag of one time step is used to compute model coefficients. For instance, if a time step is 2 seconds, then an order of "1" means that a directed link from a parent voxel to a child voxel is computed based on current voxel activity and past voxel activity 2 second ago. In order words, the model coefficients are computed based on current and past voxel activity over 1 time step (e.g., 2 seconds), although other model orders such as 2, 3, etc., can be employed.

Figure 3:
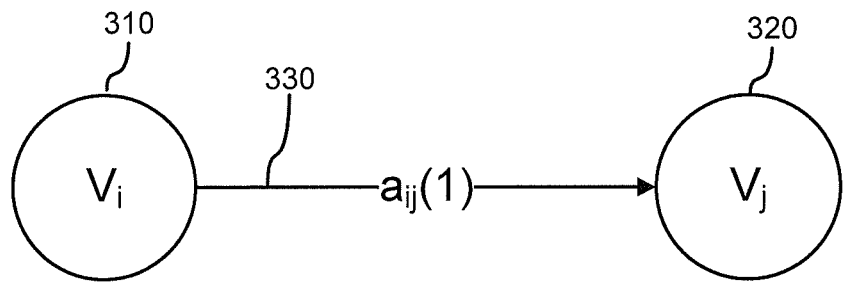
FIG. 3 depicts a directed node graph representing functional connectivity and causality of one voxel on another voxel, which is derived from modeling functional magnetic resonance image data, according to an aspect of the invention.

For instance, FIG. 3 depicts a directed node graph representing functional connectivity and causality of one voxel on another voxel, which is derived from modeling functional magnetic resonance image data according to an exemplary embodiment of the invention. In particular, FIG. 3 depicts a portion of a 3-dimensional directed node graph 300 showing a pair of voxels $V_i$ 310 and $V_j$ 320 and a directed edge $a_{ij}(1)$ 330 linking the two voxels $V_i$ 310 and $V_j$ 320. The strength of the link 330 is described by the value of $a_{ij}(1)$. If $a_{ij}(1)$ has a value of 0, this means that voxels $V_i$ 310 and $V_j$ 320 do not interact. If $a_{ij}(1)$ has a value of that is greater than 0, this means that voxel $V_i$ 310 causes the activity in voxel $V_j$ 320 to occur. The strength of this causality is greater with higher values of $a_{ij}(1)$. In this regard, the dimensionality of the full brain model may be reduced by eliminating weak links between voxel in the node graph.

Figure 4:
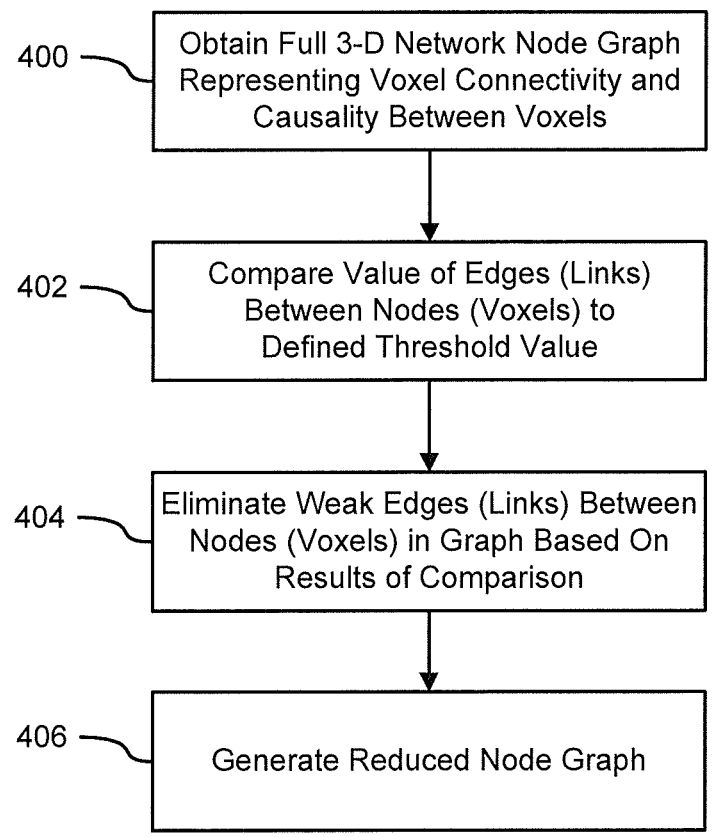
FIG. 4 is a flow diagram of a method for generating a reduced representation of a full spatio-temporal model of brain activity of a subject, according to an aspect of the invention.

For example, FIG. 4 is a flow diagram of a method for generating a reduced representation of a full spatio-temporal model of brain activity of a subject, according to an aspect of the invention. Initially, as discussed above, a first step is to obtain a full 3-D network node graph (either pre-stored or computed real time) representing voxel connectivity and causality between voxels in a fMRI scan (step 400). To reduce dimensionality of the full multi-variate model of brain activity, appropriate features are selected from the multi-variate model. In general, this process my include comparing the value of the edges (links) between nodes (voxels) to some defined threshold value (step 402). Based on the results of the comparison, weak links between voxels can be eliminated from the network node graph (step 404). A reduced network node graph can then be generated (step 406) including a set of the voxels having strong links, i.e., edge values that meet or exceed the predefined threshold.

The dimensionality of a full network node graph can be reduced (via thresholding) in one of many ways. For instance, a suitable threshold value, T, can be used to compare to the value of edges and select those edges that may be considered significant. For example, if T is set to a value of 0.5, then edges $a_{ij}(1)$ can be selected where the value of $a_{ij}(1)>0.5$. The effect of this is to eliminate weak links in the full network node graph. Another method is to first calculate the prediction power value of a given voxel, as defined above, and then threshold the prediction power value. This can result in a set of voxels, or nodes in the graph, which are selected to have high prediction power.

Indexing, Classification, Prediction

Once a reduced model representation is obtained, the model may be processed in various ways to implement functions such as database indexing, classification and/or prediction of brain activity. One way of processing the reduced representation of the full brain model is to generate a vector representation of the model for use in indexing and/or classification. In one aspect of the invention, a vector representation is based on the fact that voxels with high prediction power are typically localized in certain regions of the brain, and correspond to the specific task that the subject is performing while being scanned with fMRI. For instance, if the subject performs a motor task like tapping their fingers, then voxels of high prediction power are typically found in the motor cortex.

Figure 5:
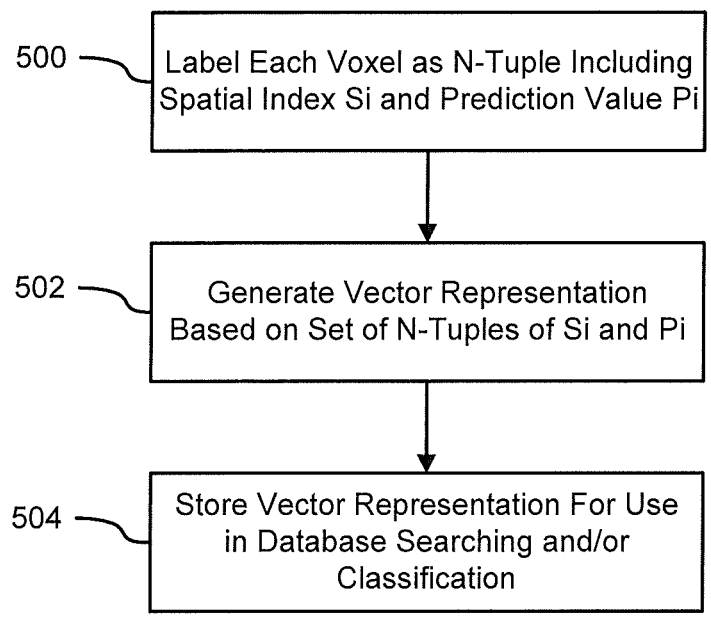
FIG. 5 is a flow diagram of a method for generating a vector representation of a reduced spatio-temporal model of brain activity of a subject for use in database searching and classification, according to an aspect of the invention.

FIG. 5 is a flow diagram of a method for generating a vector representation of a reduced spatio-temporal model of brain activity of a subject for use in database searching and classification, according to an aspect of the invention. An initial step in automatically labeling an fMRI scan is to label each voxel with a spatial index and prediction value (step 500). In particular, in one aspect of the invention, the voxels may be labeled with a 2-tuples (Si, Pi) where Si is the spatial location of the ith voxel, and Pi is the prediction power of the voxel. The spatial location Si information can be derived in many ways. For instance, the spatial location Si could refer to the specific Brodmann area that the voxel $V_i$ belongs to. Alternately, the spatial location Si can be an anatomical atlas label, such as that provided by the Montreal Neurological Institute (MNI template).

The next step is to generate a vector representation of the fMRI dataset based on the set of n-tuples (Si/Pi) associated with the voxels in that dataset (step 502). More specifically, assume that an fMRI scan gives rise to a set T of 2-tuples, (Si, Pi). One method of generating a vector representation of T is to flatten the set of 2-tuples in T according to some predefined order, say by concatenating voxels in Brodmann area 1, followed by Brodmann area 2 and so on. This defines a one-dimensional vector where each location can be mapped back to its Brodmann area, and the value at each location is the prediction power at that voxel. The vector representation this then stored in a database and may be subsequently used for database searching and/or classification (step 504).

Figure 6:
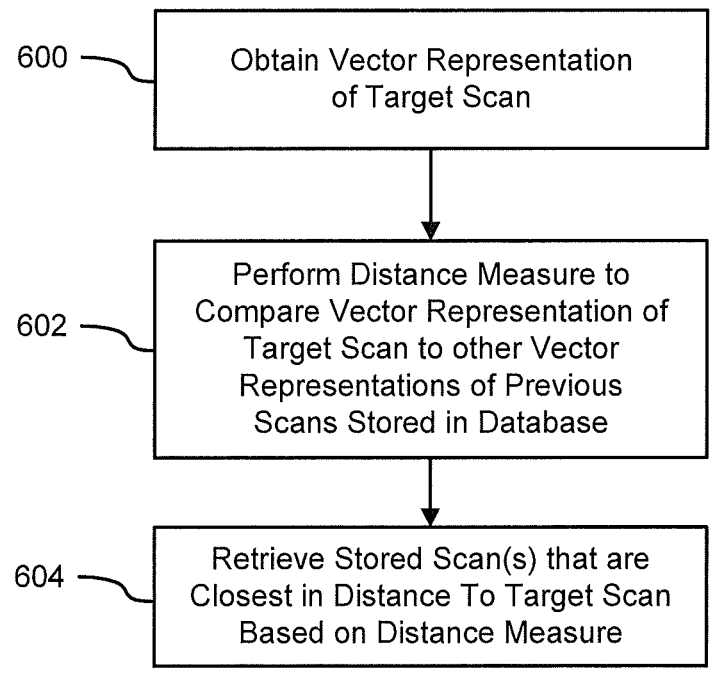
FIG. 6 is a flow diagram of a method for performing a database search using a vector representation of a reduced spatio-temporal model of brain activity of a subject, according to an aspect of the invention.

FIG. 6 is a flow diagram of a method for performing a database search using a vector representation of a reduced spatio-temporal model of brain activity of a subject, according to an aspect of the invention. An initial step is to obtain a vector representation of a target scan (step 600) using a method as discussed above with reference to FIG. 5. Assume a vector representation is denoted U1 for a dataset T1 of the target scan. Assume further that a plurality of previous scans are stored in a database, each in the form of a vector representation U as discussed above. Assume further that T2 denotes a stored dataset that is formed by labeling the voxels in the stored dataset as a set of 2-tuples (Si/Pi) to generate a vector representation U2.

To determine whether T2 (and other stored scan datasets) is similar to T1, a distance measure can be implemented to compare the vector representation U1 of the target scan dataset T1 with the vector representation U2 of the stored scan dataset T2 (step 602). There are many methods that may be implemented to define a distance measure. In one aspect of the invention, the distance between vector representations U1 and U2 can be a Euclidean distance D measure, defined as the sum of the squares of the differences between the components of U1 and U2, i.e. $\Sigma(U1_i - U2_i)^2$. This distance measure allows us to compare two fMRI scan datasets T1 and T2. If the determined distance D between U1 and U2 is small, it is determined that the scans T1 and T2 are similar, and most likely constitute similar experimental protocols. This distance measure can be used as a database search mechanism, whereby the database search engine can retrieve one or more stored scans that are closest in distance to the target fMRI scan dataset (step 604).

Figure 7:
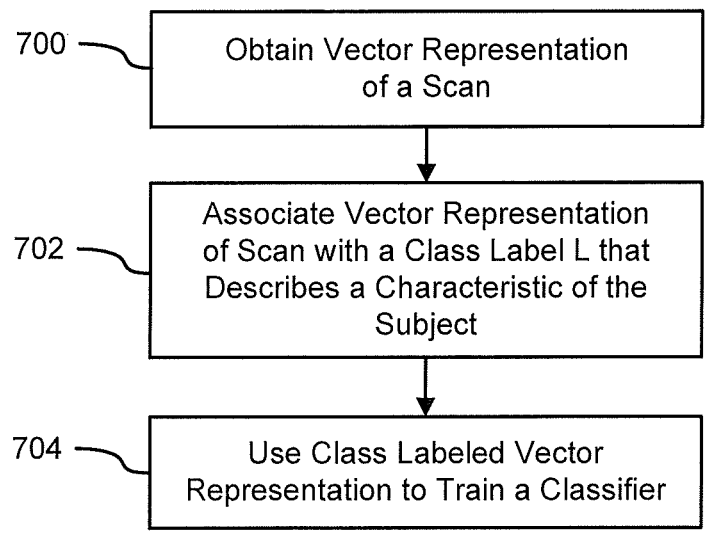
FIG. 7 is a flow diagram of a method for performing classification using a vector representation of a reduced spatio-temporal model of brain activity of a subject, according to an aspect of the invention.

In other aspects of the invention, a vector representation U for a scan dataset can be used for classification. For example, FIG. 7 is a flow diagram of a method for performing classification using a vector representation of a reduced spatio-temporal model of brain activity of a subject, according to an aspect of the invention. In particular, FIG. 7 illustrates a method for using a vector representation U of a scan dataset T to train a classifier to identify different instances of the vector U. An initial step is to obtain a vector representation U for each of one or more scan datasets (step 700). Next, each vector representation U is associated with a class label L, which may describe a characteristic (e.g., mental state) of the associated individuals (step 702). For instance, the class label L may indicate whether an individual is diseased or healthy. Thus, we obtain labeled 2-tuples, (U1, L1), (U2, L2), . . . (Un, Ln), where there are n samples of fMRI scan datasets. The labeled 2-tuples, (U1, L1), (U2, L2), . . . (Un, Ln) are then used train a suitable classifier to determine a decision boundary that can separate the different classes according to the class label L (step 704).

For instance, we can distinguish instances of class A (e.g., subjects in class A) from instances of class B (e.g., subjects in class B). One such classifier is the support vector machine, which is described in the book: The Nature of Statistical Learning Theory by Vladimir Vapnik, Springer-Verlag publisher, 1995, ISBN 0-387-98780-0, the disclosure of which is incorporated herein by reference. It is to be appreciated that other suitable classification methods may be implemented in accordance with aspects of the invention, the details of which are well understood to those of ordinary skill in the art.

Figure 8:
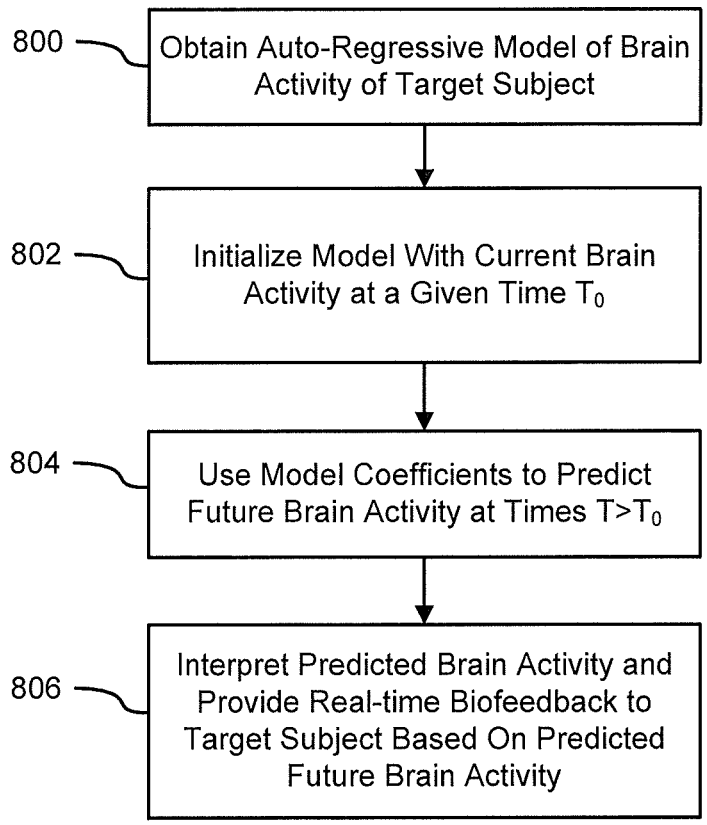
FIG. 8 is a flow diagram of a method for predicting brain activity using a reduced representation of a full spatio-temporal model of brain activity of a subject, according to an aspect of the invention.

In other aspects of the invention, an auto-regressive model can be used to predict the future time course of activities in different brain voxels. FIG. 8 is a flow diagram of a method for predicting brain activity using a reduced representation of a full spatio-temporal model of brain activity of a subject, according to an aspect of the invention. As an initial step, a full auto regressive model of brain activity is obtained for a target subject performing a given task (step 800) and reduced in form using the methods discussed above with reference to FIG. 4. Subsequently, this reduced model representation can be used to predict future brain activity for the target subject while performing the same task without having to obtain a full scan. In one aspect, when performing a prediction process, the previously generated model is retrieved from a data storage, and the model is initialized with the target subject's current brain activity at some arbitrary time instant, $T_0$, while performing the same task (step 802).

More specifically, with this process, the target subject will perform the same task that he/she previously performed when scan data was previously collected to generate the full autoregressive model of brain activity for the given task. For this process, while the subject is performing the same task, a brain scan is performed to collect some initial brain activity data that is used to initialize the model. The model coefficients are then used to predict the future brain activity of the target subject at times $T>T_0$ (step 804). More specifically, the model coefficients are used to predict how the activity in the brain of the target subject will evolve over time for the given task without having to perform a full brain scan. The model is specific to the individual subject and the activity being performed. So when the model is initialized with a current estimate of voxel activity, at time $t-T_0$, the model coefficients can be used to predict future brain activity in regions of the subject's brain at subsequent times, $T_1, T_2, T_3, \ldots$, where an accurate prediction of brain activity may be obtain for several second or tens of seconds after $T_0$, depending on the model.

The predicted brain activity can then be machine interpreted to provide real-time biofeedback to the target subject being scanned based on the predicted future brain activity (step 806). This form of biofeedback can be used for therapeutic purposes. For instance, an individual may have a stuttering problem. During an initial scan, the subject may perform a given activity that involves reading a sentence with instructions to verbally repeat the sentence aloud. During this task, a full brain scan model is generated, which may capture a sequence of brain activity that indicates a particular dysfunction in the brain processing which leads to stuttering. Thereafter, the auto-regressive model for the given subject can be used to interpret the future time course of brain activity as follows. The target subject is subsequently scanned while being shown the same specific sentence as previously shown for the full scan, and asked to read it aloud. The brain activity right after the sentence is recognized can constitute the initial condition that is applied to the previously generated model. Thereafter, the model is used to predict whether the motor cortex becomes active in the future. If the model predicts that the motor cortex will not become active and the perform is likely to stutter, corrective biofeedback can be provided to the subject, such as a light or a sound. This allows the person to take appropriate corrective action, such as controlling their breathing or articulation, to avoid or mitigate stuttering.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of fauns, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Accordingly, aspects of the invention, for example as depicted in FIGS. 1-8, can also include, as described herein, providing a system, wherein the system 100 of FIG. 1 includes distinct software modules. By way of example only, the software modules may include the model building module 110, the network map generator module 120, the indexing module 130, the prediction module 140, and the classification module 150. The modules may be adapted, for example, to perform the steps of those methods as illustrated in FIGS. 2-8.

Figure 9:
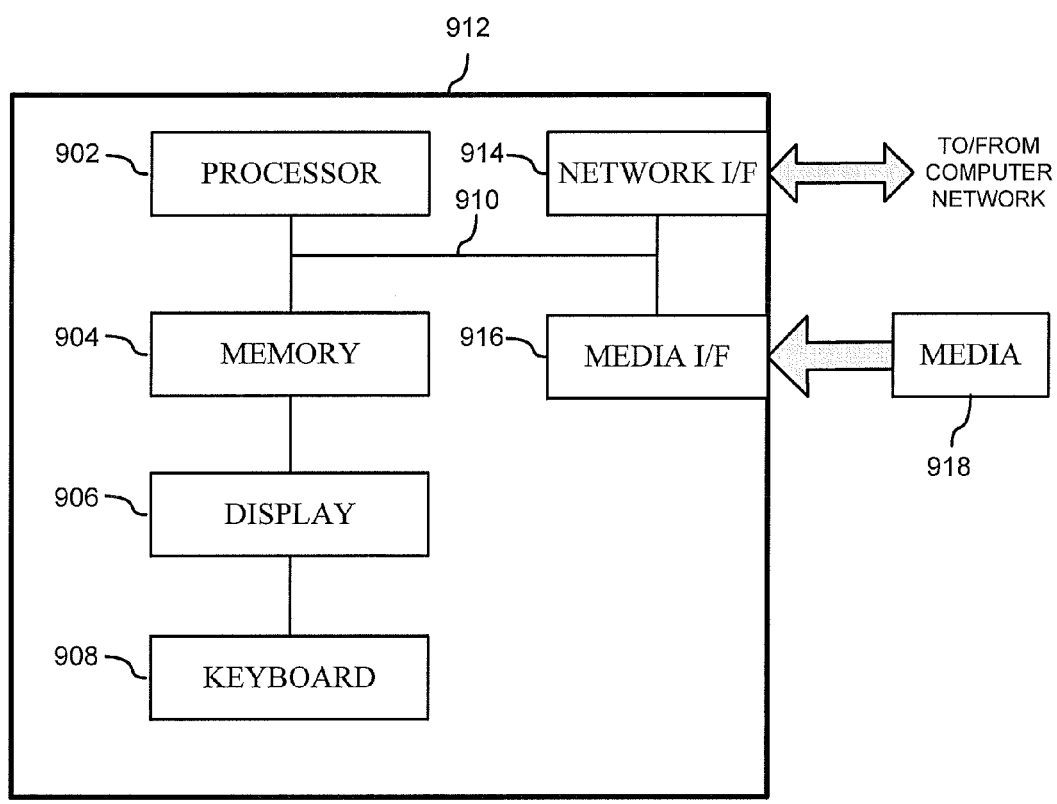
FIG. 9 depicts a computer system that may be useful in implementing one or more aspects and/or elements of the invention.

One or more embodiments can make use of software running on a general purpose computer or workstation. With reference to FIG. 9, such system 900 employs, for example, a processor 902, a memory 904, and an input/output interface formed, for example, by a display 906 and a keyboard 908. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, keyboard or mouse), and one or more mechanisms for providing results associated with the processing unit (for example, display or printer). The processor 902, memory 904, and input/output interface such as display 906 and keyboard 908 can be interconnected, for example, via bus 910 as part of a data processing unit 912. Suitable interconnections, for example via bus 910, can also be provided to a network interface 914, such as a network card, which can be provided to interface with a computer network, and to a media interface 916, such as a diskette or CD-ROM drive, which can be provided to interface with media 918.

A data processing system suitable for storing and/or executing program code can include at least one processor 902 coupled directly or indirectly to memory elements 904 through a system bus 910. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboard 908, display 906, pointing device, and the like) can be coupled to the system either directly (such as via bus 910) or through intervening I/O controllers (omitted for clarity).

Network adapters such as network interface 914 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 912 as shown in FIG. 9) running a server program. It will be understood that such a physical server may or may not include a display and keyboard.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. A method to perform an image data processing operation, comprising:
    obtaining a raw spatio-temporal dataset acquired from scanning a brain of a subject performing a given task;
    constructing a full spatio-temporal model using the raw spatio-temporal dataset, wherein the full spatio-temporal model represents brain activity that occurs in all regions of the subject's brain in response to the subject performing the given task;
    selecting model parameters from the full spatio-temporal model which meet or exceed a threshold parameter that defines a level of causal relation between voxels in the acquired dataset;
    generating a reduced model representation of the full spatio-temporal model using the selected model parameters;
    generating a vector representing the reduced model, wherein generating a vector representing the reduced model comprises:
        labeling each voxel with a spatial index Si and a prediction value Pi;
        concatenating voxels having a common spatial index Si; and
        generating a vector comprising sets of concatenated voxels and a corresponding prediction value for each set of concatenated voxels; and
    using the vector to perform an image data processing operation,
    wherein the method is performed by a computer.

2. The method of claim 1, wherein the raw spatio-temporal data comprises functional magnetic resonance imaging data.

3. The method of claim 1, wherein constructing a full spatio-temporal model comprises using a multivariate autoregressive model to generate a model of the spatio-temporal dataset.

4. The method of claim 1, wherein selecting model parameters from the full spatio-temporal model which meet or exceed a threshold parameter that defines a level of causal relation between voxels in the acquired dataset, comprises:
    obtaining a value of a causal link between a pair of voxels;
    comparing the value of the causal link to the threshold parameter;
    selecting all causal links between pairs of voxels that meet or exceed the threshold parameter; and
    eliminating all causal links between pairs of voxels that do not meet or exceed the threshold parameter.

5. The method of claim 4, wherein the threshold parameter is based on a prediction power threshold value that specifies a threshold for which brain activity in a given voxel predicts brain activity in another voxel.

6. The method of claim 1, wherein generating a reduced model representation of the full spatio-temporal model using the selected model parameters comprises generating a three-dimensional directed node graph having nodes and directed edges connecting the nodes, wherein nodes in the directed node graph represent voxels and wherein a directed edge in the directed node graph represents a causal relation between two nodes connected by the directed edge.

7. The method of claim 1, wherein using the vector to perform an image data processing operation comprises performing a database indexing operation, wherein performing a database indexing operation comprises:
    generating a vector for a target brain scan;
    using a distance measure to compare the vector for the target brain scan with one or more vectors representing corresponding brain scans stored in a database; and
    retrieving one or more stored brain scans that are close in distance to the target brain scan based on a distance measure between vectors representing said target and stored brain scans.

8. The method of claim 1, wherein using the vector to perform an image data processing operation comprises performing a classification operation, wherein performing a classification operation comprises:
    generating a vector for each of a plurality of different brain scans;
    applying a class label to each of the vectors indicating a characteristic of the associated scans; and
    training a classification system using labeled vectors of the brain scans.

9. A computer program product to perform an image data processing operation, the computer program product comprising a non-transitory computer readable storage medium having computer readable program code stored thereon, the computer readable program code comprising computer readable program code which when executed by a computer, performs the method of claim 1.

10. An apparatus to perform an image data processing operation, the apparatus comprising:
    a memory storing program instructions; and
    a processor coupled to the memory, operative to process the stored program instructions to:
    obtain a raw spatio-temporal dataset acquired from scanning a brain of a subject performing a given task;
    construct a full spatio-temporal model using the raw spatio-temporal dataset, wherein the full spatio-temporal model represents brain activity that occurs in all regions of the subject's brain in response to the subject performing the given task;
    select model parameters from the full spatio-temporal model which meet or exceed a threshold parameter that defines a level of causal relation between voxels in the acquired dataset;
    generate a reduced model representation of the full spatio-temporal model using the selected model parameters; and
    store the reduced model for use in performing an image data processing operation, wherein the image data processing operation includes one of image indexing, classification, and predicting future brain activity,
    wherein the processor is further operative to process the stored program instructions to:
        generate a vector representing the reduced model, wherein generating a vector comprises labeling each voxel with a spatial index Si and a prediction value Pi, concatenating voxels having a common spatial index Si, and generating a vector comprising sets of concatenated voxels and a corresponding prediction value for each set of concatenated voxels; and
        use the vector to perform image indexing and image classification.

11. The apparatus of claim 10, wherein the processor is operative to process the stored program instructions to predict future activity by:
- obtaining the stored reduced model;
- initializing the reduced model with current brain activity data derived from a scan of the subject's brain while the subject is performing the same given task; and
- predicting future brain activity of the subject using the reduced model based on the current brain activity data initializing said reduced model.

12. The apparatus of claim 10, wherein the processor is operative to process the stored program instructions to use the vector to perform an image indexing operation by generating a vector for a target brain scan, using a distance measure to compare the vector for the target brain scan with one or more vectors representing corresponding brain scans stored in a database, and retrieving one or more stored brain scans that are close in distance to the target brain scan based on a distance measure between vectors representing said target and stored brain scans.

13. The apparatus of claim 10, wherein the processor is operative to process the stored program instructions to use the vector to perform an image classification operation by generating a vector for each of a plurality of different brain scans, applying a class label to each of the vectors indicating a characteristic of the associated scans, and training a classification system using labeled vectors of the brain scans.

* * * * *